United States Patent
McMichael

(10) Patent No.: US 6,267,116 B1
(45) Date of Patent: Jul. 31, 2001

(54) METHOD AND SYSTEM FOR USE IN TREATING A PATIENT WITH ANY DRUG TO OPTIMIZE THERAPY AND PREVENT AN ADVERSE DRUG

(75) Inventor: John McMichael, Wexford, PA (US)

(73) Assignee: The RxFiles Corporation, Nokomis, FL (US)

( * ) Notice: Subject to any disclaimer, the term of this patent is extended or adjusted under 35 U.S.C. 154(b) by 0 days.

(21) Appl. No.: 09/348,592

(22) Filed: Jul. 6, 1999

(51) Int. Cl.[7] ................................................ A61B 19/00
(52) U.S. Cl. ........................................ 128/898; 600/300
(58) Field of Search ................ 128/897–98; 600/300, 600/308, 347, 364–366, 368

(56) References Cited

U.S. PATENT DOCUMENTS

| | | | |
|---|---|---|---|
| 5,365,948 | * 11/1994 | McMichael | 128/898 |
| 5,542,436 | * 8/1996 | McMichael | 128/897 |
| 5,694,950 | * 12/1997 | McMichael | 128/898 |

* cited by examiner

*Primary Examiner*—John P. Lacyk
(74) *Attorney, Agent, or Firm*—Irving M. Weiner; Pamela S. Burt; Weiner & Burt, P.C.

(57) ABSTRACT

A method and system for use in treating a patient receiving any drug to optimize therapy and to prevent an adverse drug response. This system employs surrogate markers or indicators, including blood levels of drug, to determine the next required dose for a patient. Before surrogate markers are employed as a percent change in status, virtually any indicator can be used. Surrogate markers could include any measure the effectiveness of a drug's action. Given the effectiveness of the drug's action, relative to the surrogate markers, a change in drug dose is calculated by the system. Conversely, by employing this system, one could determine the expected result of a drug dose change on the surrogate markers.

15 Claims, 2 Drawing Sheets

METHOD AND SYSTEM FOR USE IN TREATING A PATIENT WITH ANY DRUG TO OPTIMIZE THERAPY AND PREVENT AN ADVERSE DRUG

A portion of the disclosure of this patent document contains material which is the subject of copyright protection. The copyright owner has no objection to the facsimile reproduction by anyone of the patent disclosure as it appears in the public patent files of the United States Patent and Trademark Office, but otherwise reserves all other rights in the copyrighted material.

FIELD OF THE INVENTION

The present invention relates to a method and system for use in treating a patient with any drug to optimize drug therapy and to prevent an adverse drug response. The present invention can utilize either drug levels or other surrogate markers to determine the effectiveness of the dosing regimen and, if necessary, to suggest a new more optimal drug dose.

BACKGROUND OF THE INVENTION

When a patient begins taking any medication for a length of time, a titration of the amount of drug taken by the patient is necessary in order to achieve the optimal benefit of the drug and at the same time to prevent any undesirable side effects that taking too much of the drug could produce. Thus, there is a continuous balance between taking enough drug in order to gain the benefits from that drug and at the same time not taking so much drug as to illicit a toxic event.

There is large inter-individual variability in the patient pharmacokinetics of drugs. What may be an appropriate drug dose for one individual, may be too much or too little for another. Prior to this invention a physician was required to estimate the correct drug dosage for a patient and then to experiment with that dosage, usually by trial and error, until the correct dosage was achieved. Likewise, the FDA labeling of a drug suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate drug dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some drugs, but because the models are static and cannot adapt themselves to changes within a population or a patient, they are once again undesirable for dynamically determining drug dosages.

Expert systems have been developed using similar technology to predict drug dosages for immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual immunosuppressant drug. As it stands, these inventions cannot be applied to other drugs and do not have a non-linear feedback loop mechanism.

SUMMARY OF THE INVENTION

According to the present invention, patient dosing occurs through a cyclic series of events, depicted in flow chart form in FIG. 1. After an initial examination, an initial dose of a drug (therapeutic agent) is prescribed and administered by a physician for a patient. The initial dose is based on the FDA recommended dosage found on the drug label. The drug dose is further refined upon repeated dosing by the physician based on the patient's response to the drug. Too much drug could cause the patient to experience toxic drug effects, and the drug dose would need to be reduced. Too little drug could cause the patient not to receive the benefit the drug therapy could offer, and the dosage would need to be increased.

The preferred embodiment of the invention requires that a physician determine the percentage of response by the patient to the drug based on the surrogate markers for that drug. A relationship is then employed which uses the input parameters described above to determine the next dose for the patient. This invention has two preferred embodiments; one which uses actual numerical surrogate markers to calculate a dose, and another embodiment that uses percentages as the numerical input for the surrogate markers.

DETAILED DESCRIPTION OF THE INVENTION

The present invention provides a method and system for use in treating a patient receiving any drug to optimize therapy and to prevent an adverse drug response. This system employs surrogate markers or indicators, including blood levels of drug, to determine the next required dose for a patient. Because the surrogate markers are employed as a percent change in status, virtually any indicator can be used. Surrogate markers could include any measure of the effectiveness of a drug's action. Given the effectiveness of the drug's action, relative to the surrogate markers, a change in drug dose is calculated by the system. Conversely, by employing this system, one could determine the expected result of a drug dose change on the surrogate markers.

Figure 1:
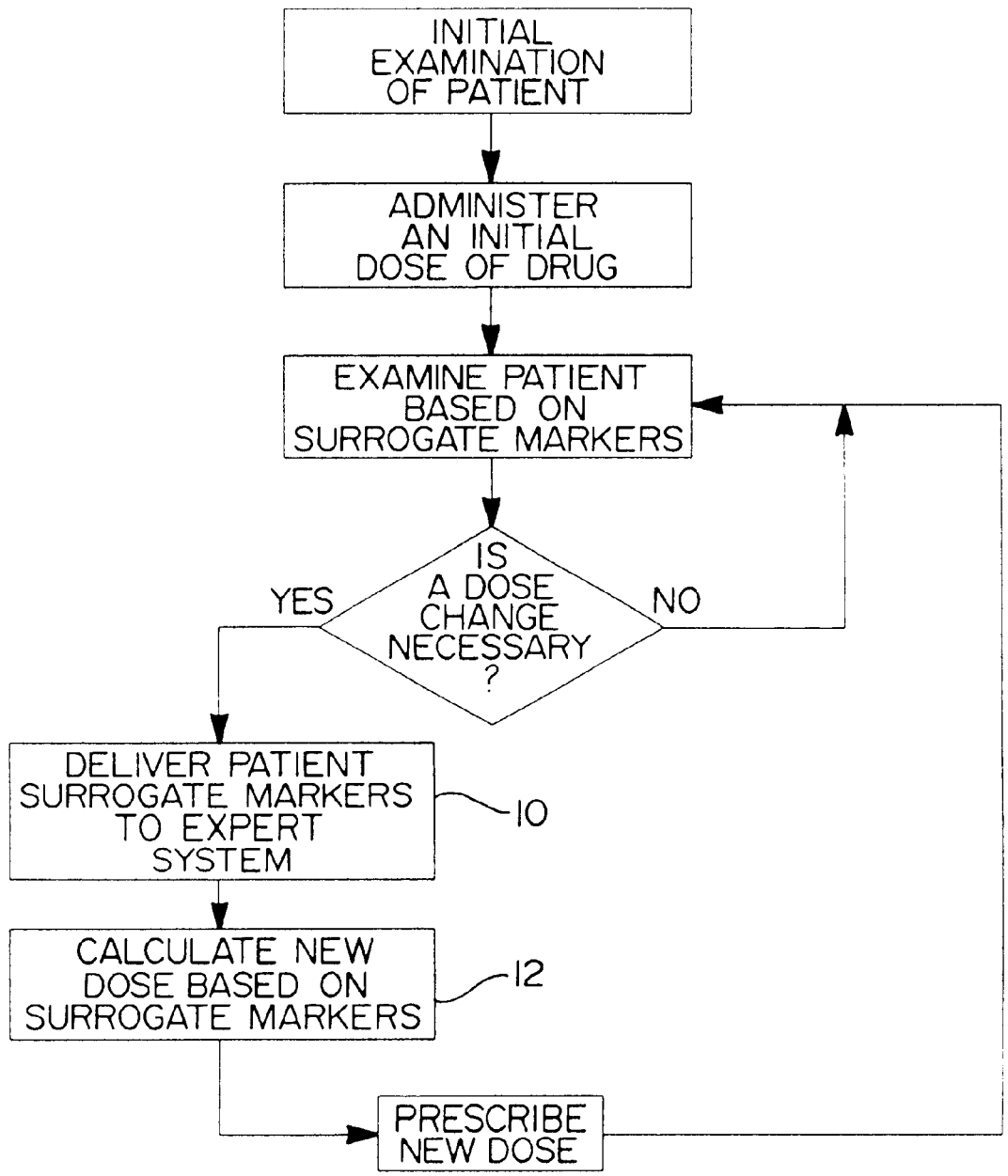
FIG. 1 shows a flow chart of the process by which revised doses of a drug are determined, according to the method of the invention described herein.

A method of this invention for use in treating a patient receiving any drug to optimize therapy and to prevent an adverse drug response can be implemented in two different embodiments, two of which will each be described separately. FIG. 1 shows a flow chart of the overall process of treating a patient using this expert system. The actual expert system, however, performs only the steps shown in blocks 10 and 12 of the flow chart.

Figure 2:
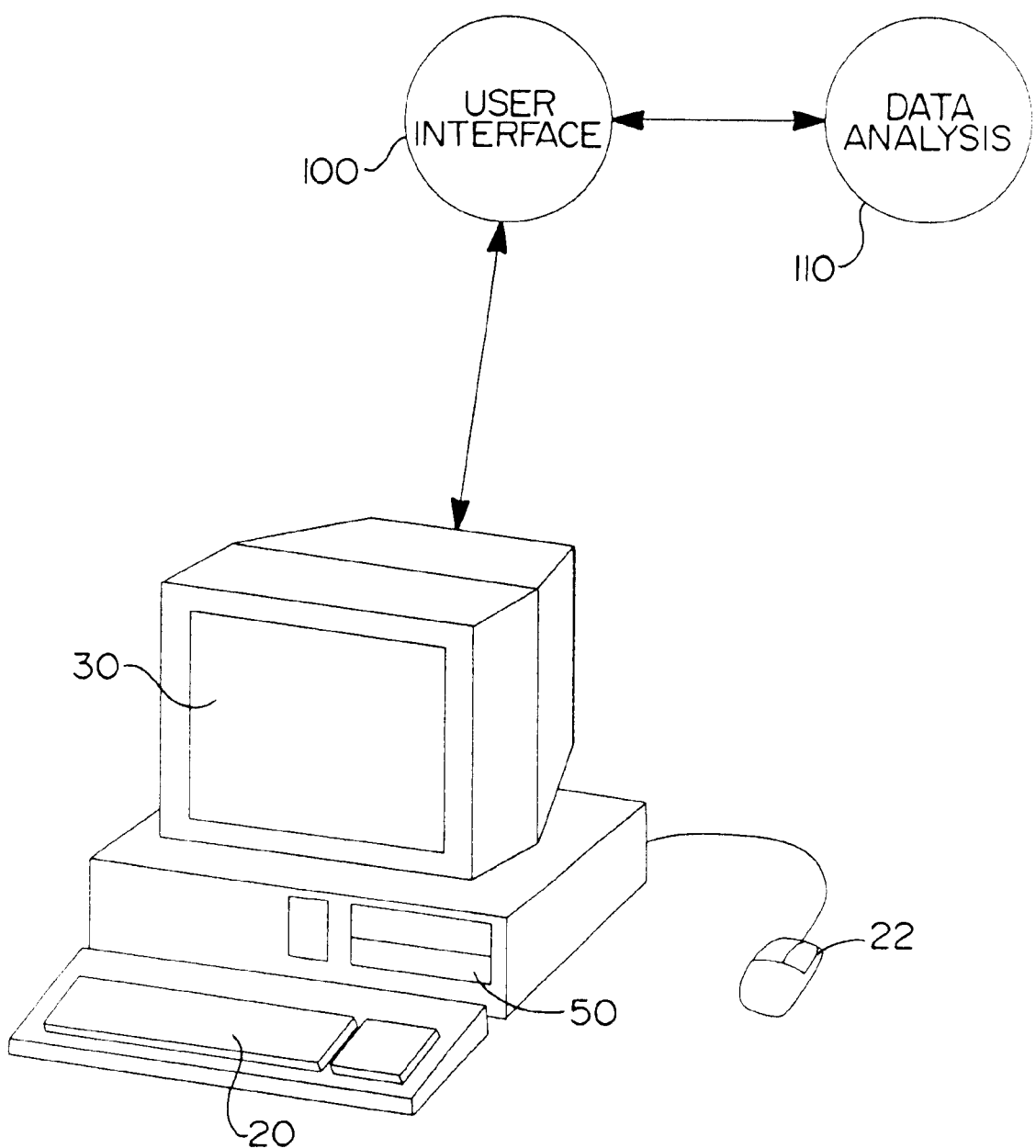
FIG. 2 shows an apparatus for use in calculating revised doses of a drug according to the present invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current drug dose, the maximal dose range for the drug, and the percent response of the patient based on the surrogate markers used to monitor the drug. Also characterized is the patient's response to the last dosing cycle as well as a dose response constant. This allows the expert system to individualize the patient dosing based on the patient's individual response to the drug. The system calculates a revised dosage based on the data input by the physician. The software portion of the invention includes a user interface portion 100 to receive the input data and to output the revised dosage information, and a data analysis portion 110, which calculates the new dosage information based on the input data Numerical Surrogate Markers Embodiment A physician prescribes a drug for a patient based on the FDA recommended dose on the label of the drug. The physician then re-evaluates the patient, usually daily, either in person or remotely depending on the agent being prescribed. During the subsequent evaluations by the physician, the surrogate markers are monitored and sequentially compared to determine if there are any toxicities associated with the drug. Also the numerical markers will evaluated to see if the desired effect of the drug is being achieved. Based on this evaluation by the physician, the current drug dose, the current drug numerical marker, the desired drug numerical marker, and the previous drug numerical marker are then input into the embodiment and the new drug dose is calculated based on the equation:

$$NDD=CDD-\{[<(CDNM-DDNM)/CDNM>/<1+(CDD/HIGH)>]\times CDD\}+LV$$

where:

$$LV=\{(RESP\times CDD)\times[(1+D)-(1+E)]/abs(1+D)\}/[1.3\char`\^(CDD/HIGH)]$$

$$E=(CDNM-PDNM)$$

$$D=(DDNM-PDNM)$$

$$RESP=RESPONSE/100$$

and wherein:

NDD=New Drug Dose
CDD=Current Drug Dose
CDNM=Current Drug Numerical Marker
DDNM=Desired Drug Numerical Marker
PDNM=Previous Drug Numerical Marker
HIGH=The input paramater that is the high dose range for a particular drug.
RESPONSE=Total dose available for individualizing patient dose.
abs=The absolute value of
$\char`\^$=Raised to the $n^{th}$ power.

Percentage Surrogate Markers Embodiment

In this preferred embodiment, a physician prescribes a drug for a patient based on the FDA recommended dose on the label of the drug. The physician then re-evaluates the patient, usually daily, either in person or remotely depending on the agent being prescribed. During the subsequent evaluations by the physician, the surrogate markers are monitored and sequentially compared to determine if there are any toxicities associated with the drug. Also the surrogate markers are evaluated to see if the desired effect of the drug is being achieved. Based on this evaluation by the physician, the current drug dose, and the percent response of the patient to the last dosing based on a surrogate marker are then input into the system and the new drug dose is calculated based on the equation:

$$NDD=CDD-\{[<(PDR-100)/PDR>/<1+(CDD/HIGH)>]\times CDD\}+LV$$

where:

$$LV=\{(RESP\times CDD)\times[(100-RES)\times 0.01]\}/[1.3\char`\^(CDD/HIGH)]$$

$$RESP=RESPONSE/100$$

and wherein,

NDD=New Drug Dose
CDD=Current Drug Dose
PDR=Percent response of patient to surrogate marker
RES=Percent response of patient to last dosing based on surrogate marker
HIGH=The input parameter that is the high dose range for a particular drug.
RESPONSE=Total dose available for individualizing patient dose.
$\char`\^$=Raised to the $n^{th}$ power.

This cycle of repeated re-evaluation of the numerical surrogate markers is continued as long as the patient is required to take the drug.

Two embodiments of the invention have been described, one using numerical markers, and one using a percentage surrogate marker. Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof

I claim:

1. A method for calculating a revised dose of a drug for a patient using said drug, comprising the steps of:

accepting as a first input the patient's current drug dose;

accepting as a second input a maximum dose of the drug;

accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

2. The method of claim 1, wherein said determining step includes determining said revised dose based on the equation $$RDD=CDD-\{[<(PDR-100)/PDR>/<1+(CDD/HIGH)>]\times CDD\}+LV$$

where:

$$LV=(RESPONSE\times CDD)\times[(100-RES)\times 0.01]/[1.3\char`\^(CDD/HIGH)]$$

and wherein:

RDD=Revised Drug Dose
CDD=Current Drug Dose
PDR=Percent response of patient to surrogate marker
RES=Percent response of patient to last dosing based on surrogate marker
HIGH=The input parameter that is the high dose range for a particular drug
RESPONSE=Percent of total dose available for individualizing patient dose 1.3$\char`\^$(*CDD/HIGH*)=1.3 raised to an exponent of (*CDD/HIGH*).

3. A method for calculating a revised dose of a drug for a patient using said drug, comprising the steps of:

accepting as a first input the patient's current drug dose;

accepting as a second input the maximum dose of the drug;

accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor.

4. The method of claim 3, wherein said calculating step includes calculating said revised dose based on the equation $$RDD=CDD-\{[<(CDNM-DDNM)/CDNM>/<1+(CDD/HIGH)>]\times CDD\}+LV$$

where:

$$LV=\{(RESPONSE\times CDD)\times[(1+D)-(1+E)]/abs(1+D)\}/[1.3\char`\^(CDD/HIGH)]$$

$$E=(CDNM-PDNM)$$

$$D=(DDNM-PDNM)$$

and wherein:

RDD=Revised Drug Dose

CDD=Current Drug Dose

CDNM=Current Drug Numerical Marker

DDNM=Desired Drug Numerical Marker

PDNM=Previous Drug Numerical Marker

HIGH=The input parameter that is the high dose range for a particular drug

RESPONSE=Percent of total dose available for individualizing patient dose $1.3\char`\^(CDD/HIGH)$=1.3 raised to an exponent of $(CDD/HIGH)$.

5. A method for determining a dose of a drug for a patient, comprising the steps of:

administering an initial dose of said drug to the patient;

evaluating the patient to monitor and characterize one or more numerical surrogate markers;

determining, based on said numerical surrogate markers, if a dose change for said drug is necessary; and calculating a revised dose as a function of said current dose minus the ratio of a percent response of the patient and the ratio of said current dose to said maximum dose plus the percent of individual patient response multiplied by a response factor.

6. A method for determining a dose of a drug for a patients comprising the steps of:

administering an initial dose of drug to the patient;

examining the patient to monitor and to characterize one or more numerical surrogate markers;

determining if a dose change is necessary; and calculating a revised dose as a function of said current dose minus the ratio of the change in numerical markers and the ratio of said current dose to said maximum dose plus the percent of individual patient response multiplied by a response factor.

7. A method for calculating a revised dose of a drug for a patient, comprising the steps of:

accepting as input the patient's current drug dose;

accepting as input the maximum dose of the drug;

accepting as input the percent response of the patient based on surrogate markers; and calculating a revised dose, wherein said revised dose is a function of said current dose, said maximum doses and said percent response of the patient based on said surrogate markers.

8. A method for calculating a revised dose of a drug for a patient, comprising the steps of:

accepting as input a patient's current drug dose;

accepting as input a maximum dose of the drug;

accepting as input the previous, current and desired values of one or more numerical markers indicating the response of the patient; and calculating a revised dose, wherein said revised dose is a function of said current dose, said maximum dose, and said previous, currents and desired values of said numerical markers.

9. A storage device having stored thereon an ordered set of instructions which, when executed by a computer, performs a predetermined method, comprising:

first means for accepting as input a patient's current drug dose;

second means for accepting as input a maximum dose of the drug;

third means for accepting as input a percent response of said patient based on surrogate markers; and fourth means for calculating a revised dose, wherein said revised dose is a function of said current dose minus the ratio of a percent response of the patient and the ratio of said current dose to said maximum dose plus the percent of individual patient response multiplied by a response factor.

10. A storage device having stored thereon an ordered set of instructions which, when executed by a computer, performs a predetermined method, comprising:

first means for accepting as input a patient's current drug dose;

second means for accepting as input the maximum dose of the drug;

third means for accepting as input one or more numerical markers indicating the response of the patient; and fourth means for calculating a revised dose, wherein said revised dose is a function of said current dose minus the ratio of the change in numerical markers and the ratio of said current dose to said maximum dose plus the percent of individual patient response multiplied by a response factor.

11. An apparatus for calculating a revised dose of a drug for a patient, comprising:

means for accepting as input one or more markers which indicate said patient's response to a dose of a drug;

means for accepting as input the patient's current drug dose;

means for accepting as input the maximum dose of the drug; and means for calculating a revised dose of the drug as a function of said markers, said current drug dose, and said maximum drug dose.

12. The apparatus of claim 11, wherein said markers are actual numerical markers.

13. The apparatus of claim 12, wherein said revised dose is calculated by the following equation $$RDD=CDD-\{[<(CDNM-DDNM)/CDNM>/<1+(CDD/HIGH)>]\times CDD\}+LV$$

where:

$$LV=\{(RESPONSE\times CDD)\times[(1+D)-(1+E)]/abs(1+D)\}/[1.3\char`\^(CDD/HIGH)]$$

$$E=(CDNM-PDNM)$$

$$D = (DDNM - PDNM)$$

and wherein:

RDD=Revised Drug Dose
CDD=Current Drug Dose
CDNM=Current Drug Numerical Marker
DDNM=Desired Drug Numerical Marker
PDNM=Previous Drug Numerical Marker
HIGH=The input parameter that is the high dose range for a particular drug
RESPONSE=Percent of total dose available for individualizing patient dose
$1.3\char`\^(CDD/HIGH)$=1.3 raised to an exponent of $(CDD/HIGH)$.

14. The apparatus of claim 11, wherein said markers are surrogate markers representing a percent response of the patient to the drug.

15. The apparatus of claim 14, wherein said revised dose is calculated by the following equation $$RDD = CDD - \{[<(PDR-100)/PDR>/<1+(CDD/HIGH)>] \times CDD\} + LV$$

where:

$$LV = (RESPONSE \times CDD) \times [(100 - RES) \times 0.01]/[1.3\char`\^(CDD/HIGH)]$$

and wherein:

RDD=Revised Drug Dose
CDD=Current Drug Dose
PDR=Percent response of patient to surrogate marker
RES=Percent response of patient to last dosing based on surrogate marker
HIGH=The input parameter that is the high dose range for a particular drug
RESPONSE=Percent of total dose available for individualizing patient dose
$1.3\char`\^(CDD/HIGH)$=1.3 raised to an exponent of $(CDD/HIGH)$.

\* \* \* \* \*

UNITED STATES PATENT AND TRADEMARK OFFICE
CERTIFICATE OF CORRECTION

PATENT NO.    : 6,267,116 B1
DATED         : July 31, 2001
INVENTOR(S)   : McMichael, John It is certified that error appears in the above-identified patent and that said Letters Patent is hereby corrected as shown below:

<u>Title page, Item [54] and Column 1, line 4,</u>
Title, after "ADVERSE DRUG" insert -- RESPONSE --;

<u>Column 3,</u>
Line 41, change "Total" to -- percent of total --;

<u>Column 4,</u>
Line 9, change "Total" to -- percent of total --;
Line 58, the material after "patient dose" should be moved to a new line.

Signed and Sealed this

Twenty-sixth Day of November, 2002

*Attest:*

JAMES E. ROGAN
*Attesting Officer*    *Director of the United States Patent and Trademark Office*